United States Patent [19]

Sagai et al.

[11] Patent Number: 4,960,877

[45] Date of Patent: Oct. 2, 1990

[54] DNA HAVING GENETIC INFORMATION OF L-α-GLYCEROPHOSPHATE OXIDASE AND APPLICATION THEREOF

[75] Inventors: Hitoshi Sagai, Mishima; Keiko Nogata; Mamoru Takahashi, both of Shizuoka, all of Japan

[73] Assignee: Toyo Jozo Co., Ltd., Shizuoka, Japan

[21] Appl. No.: 283,463

[22] Filed: Dec. 12, 1988

[30] Foreign Application Priority Data

Dec. 15, 1987 [JP] Japan .................... 62-317129

[51] Int. Cl.$^5$ .................... C12N 15/53; C12N 1/21
[52] U.S. Cl. .................... 536/27; 435/252.3; 435/252.31; 435/252.33; 435/69.1; 935/69; 935/73; 935/74; 935/60; 935/14
[58] Field of Search ............ 435/68, 190, 172.3; 536/27

[56] References Cited

U.S. PATENT DOCUMENTS 4,275,161  6/1981  Misaki et al. .................... 435/190
4,463,095  7/1984  Emi et al. .................... 435/190

FOREIGN PATENT DOCUMENTS 3244129  11/1983  Fed. Rep. of Germany .
2431534  2/1980  France .

OTHER PUBLICATIONS

*The Journal of Biological Chemistry*, vol. 254, pp. 2710–2715 (1979).
*The Journal of Biological Chemistry*, vol. 261, pp. 14396–14407 (1986).
Search Report for French Patent Application 88 16486.
CA 110: 19322t, A Genetic Analysis of the α Glycerophosphate Oxidase Locus in D. Melanogaster, Davis et al.

*Primary Examiner*—Richard A. Schwartz
*Assistant Examiner*—S. Nolan
*Attorney, Agent, or Firm*—Oblon, Spivak, McClelland, Maier & Neustadt

[57] ABSTRACT

DNA having a base sequence encoding a specified amino acid sequence of a polypeptide constituting an L-α-glycerophosphate oxidase (GPO) is disclosed. A polypeptide having the specified amino acid sequence can be produced by inserting the DNA into a plasmid, culturing a transformant produced by introducing this plasmid into a host microorganism which is selected from microorganisms belonging to *Escherichia coli, Bacillus subtilis,* or *Saccharomyces cerevisiae.* The GPO is useful for the quantitative analysis of triglyceride, glycerine, etc., and the determination of lipase activity, when used in combination with other enzymes such as lipase, glycerol kinase, or the like, or with an ATP reagent.

8 Claims, 1 Drawing Sheet

FIG. 1

DNA HAVING GENETIC INFORMATION OF L-α-GLYCEROPHOSPHATE OXIDASE AND APPLICATION THEREOF

BACKGROUND OF THE INVENTION

1. Field of the Invention

This invention relates to DNA comprising genetic information for L-α-glycerophosphate oxidase, a transformant possessing said DNA, a polypeptide produced by causing said transformant to express the genetic information of said DNA, and a process for producing said L-αglycerophosphate oxidase.

2. Description of the Background

L-α-glycerophosphate oxidase is an enzyme catalyzing an enzymatic reaction for producing dihydroxyacetone phosphate and one mole of hydrogen peroxide from L-αglycerophosphate and one mole of oxygen according to the following reaction formula:

Since L-α-glycerophosphate oxidase (hereinafter abbreviated as "GPO") is an oxidase having as its substrate L-α-glycerophosphate, as can be seen from the above reaction formula, it can be used for the quantitative determination of L-α-glycerophosphate. In addition, this enzyme, when used in combination with other enzymes such as lipase, glycerol kinase, or the like, or with an ATP reagent, provides a simple and specific determination method for the components involving the reaction, such as lipase activity, triglyceride, glycerine, ATP, and the like. Because of these reasons, L-α-glycerophosphate oxidase is a major enzyme for biochemical quantitative analysis which is to replace conventional, non-specific chemical quantitative analysis. Thus, the enzyme is very useful in the field of clinical diagnosis as well as in the field of research.

GPO has long been known to exist in the natural world. For instance, the enzyme has been reported to exist in microorganisms belonging to genera such as Streptococcus, Lactobacillus, Leuconostock, Pediococcus, and Aerococcus [*Archives of Biochemistry and Biophysics*, 88, 250 (1960); Japanese Patent Laid-open No. 72,892/1978; and Japanese Patent Laid-open No. 15,746/1980].

However, the production of GPO by these conventionally known GPO producing-microorganisms has had several problems. Specifically, all of the known GPO producing-microorganisms achieved only a low GPO productivity. GPO producing-microorganisms belonging to the strain *Streptococcaceae* and the strain *Lactobacilleceae* require the addition of a substance inducing the production of GPO, such as glycerol, ascorbic acid, α-keto acid, or the like. In addition, the elimination of other enzymes and the like which exist together with GPO in the product of these microorganisms is very difficult. Because of these problems a high quality GPO could only be produced at an extremely high cost, and this has thus prevented GPO from being widely used as a reagent for research purposes and for clinical diagnosis.

In addition, there have been no reports concerning the detailed primary structure of the GPO gene, nor about the primary structure of the amino acid sequence for the protein constituting GPO.

The present inventors have undertaken extensive studies for promoting the productivity of GPO and for reducing the amount of other co-existing enzymes (contaminant enzymes) contained in the product. As a result, the inventors have succeeded in separating the GPO gene and in the determination of its primary structure. The inventors have further established, through the application of genetic engineering techniques, a process for producing GPO at a high productivity and without using any additives to induce GPO production in the production medium.

SUMMARY OF THE INVENTION

Accordingly, an object of this invention is to provide DNA having a base sequence encoding an amino acid sequence of a polypeptide constituting L-α-glycerophosphate oxidase (GPO), a transformant having said DNA, a polypeptide which has GPO activity and is produced through culturing said transformant, a GPO with superior physicochemical characteristics, as well as a process for producing such a GPO.

Other objects, features and advantages of the invention will hereinafter become more readily apparent from the following description.

DETAILED DESCRIPTION OF THE INVENTION AND PREFERRED EMBODIMENTS

The DNA of the present invention can be prepared, for example, by the following method through the application of genetic engineering techniques. DNA of a microorganism which is the GPO gene donor and has GPO producing capability is first separated and purified. This DNA is digested using ultrasonic waves or a restriction endonucleases. This digested DNA and an expression vector DNA, which is rendered linear, are joined with a DNA ligase or the like at the blunt or cohesive ends of the two DNAs to form a closed circle. The recombinant DNA vector thus obtained is introduced into a reproducible host microorganism. Microorganisms having said recombinant DNA vector selected by means of screening using the vector marker and the GPO activity as indicators are cultured. Said recombinant DNA vector is then separated from the cultured cells and purified. The DNA possessing the GPO genetic information of the present invention is then separated from said recombinant DNA vector.

Any microorganisms having GPO producing capability can be used as a GPO gene-donating microorganism for the purpose of this invention. Examples are GPO-producing microorganisms belonging to the genus Streptococcus disclosed in Japanese Patent Application Laid-open Nos. 72892/1978, 15746/1980, 165789/1978, and the like, including the strains *Streptococcus faecium* F-24, *Streptococcus faecalis* 10C1, *Streptococcus faecium* ATCC 12755, *Streptococcus faecium* ATCC 8043, *Streptococcus faecalis* ATCC 19488, *Streptococcus cremoris* NRRL B684, and the like; GPO-producing microorganisms belonging to the genus Pediococcus, including the strains *Pediococcus cerevisiae* ATCC 8042, (*Pediococcus acidilactici* ATCC 8042), *Pediococcus cerevisiae* ATCC 8081 (*Pediococcus acidilactici* ATCC 8081), *Pediococcus cerevisiae* IFO 12230 (*Pediococcus pentosaceus* IFO 12230), *Pediococcus acidilactici*

IFO 3885, *Pediococcus pentosaceus* IFO 12318, *Pediococcus parvulus* IFO 12235 (*Pediococcus parvulus* IFO 19371), *Pediococcus homari* IFO 12217 (*Pediococcus sp* IFO 12217), *Pediococcus urinae-equi* ATCC 29722 (*Pediococcus urinae-equi* IFO 12173), and the like; GPO-producing microorganisms belonging to the genus Lactobacillus, including the strains *Lactobacillus delbruckii* NRRL B445 (*Lactobacillus casei subsp rhamnosus* ATCC 10863), *delbruckii* NRRL B445 *Lactobacillus fermentum* NRRL 8338, *Lactobacillus leichmannii* ATCC 4797, and the like; GPO-producing microorganisms belonging to the genus Leuconostoc, including the strain *Leuconostoc mesenteroides* and the like; and GPO-producing microorganisms belonging to the genus Aerococcus, including the strains *Aerococcus viridance* IFO 12219, *Aerococcus viridance* IFO 12317, and the like. Among these, GPO-producing microorganisms belonging to the genus Streptococcus are preferable.

The present inventors have further undertaken extensive research for the production of a GPO exhibiting no defect inherent to any known enzymes, and discovered that a novel strain GPOS-53 belonging to the genus Streptococcus, which was isolated from the soil of a ranch at Yamaguchi, Susono City, Shizuoka Prefecture, Japan, produced a GPO having a superior physicochemical characteristics. This strain GPOS-53 is a particularly preferable microorganism for producing said GPO gene.

Taxonomic characteristics of this novel strain GPOS-53 are as follows:

I. Growth conditions in various culture media (culturing at 28°–30° C.)

(1) Slant medium culturing (nutrient agar medium-+yeast extract 0.2%)
  Growth are filiform, but rather weakly, colored creamy or milky white. Soluble pigment substance is not produced.

(2) Plate medium culturing (nutrient agar medium-+yeast extract 0.2%)
  Colonies are circular, convex shaped, and creamy or milky white color. Soluble pigment substance is not produced.

(3) Liquid medium (Triptic Soy Broth, manufactured by Difco Co.)
  Cells grow well with the broth turning turbid. The cells then precipitate and the supernatant becomes clear.

(4) BCP milk culturing
  The culture broth turns acidic.

II. Morphological characteristic

Cells are spherical or ovoid. There are single, non-linked cells, two-chained cells, and long-chained cells. The cells are non-motile and do not form spore. The size of the cells is 0.8 to 1.0 μm.

| III. Physiological and biochemical characteristics (in descriptions hereafter "+" denotes positive, "−" denotes negative, and "(+)" denotes weakly positive. | |
|---|---|
| Gram staining | + |
| KOH reaction | − |
| Acid-fast staining | − |
| Capsule formation | − |
| OF test (Hugh Leifson) | F |
| Growth under anaerobic conditions | + |
| Growth temperature 45° C. | + |
| 30° C. | + |
| 10° C. | + |

| III. Physiological and biochemical characteristics (in descriptions hereafter "+" denotes positive, "−" denotes negative, and "(+)" denotes weakly positive. | |
|---|---|
| Salt resistance: | |
| at NaCl conc. 0% | + |
| 5.0% | + |
| 6.0% | − |
| Growth at pH 9.5 | + |
| pH 8.0 | + |
| pH 4.0 | + |
| Growth in a methylene blue milk medium | + |
| Catalase production | − |
| Oxidase production | − |
| Urease production (for both SSR and Chris) | − |
| Gelatin decomposition | − |
| Casein decomposition | + |
| Esculin hydrolysis | + |
| Hippurate decomposition (API 20 STREP) | + |
| Cellulose decomposition | − |
| Arginine decomposition | + |
| Indol production | − |
| Hydrogen sulfide production | − |
| Acetoin production (NaCl) | + |
| MR Test | + |
| Nitrate reduction | − |
| Denitrification | − |
| Utilization test | |
| Citric acid (for both Simons and Chris) | − |
| Malic acid (for Simons) | − |
| (for Chris) | + |
| Propionic acid (for Simons) | − |
| Malonic acid (for Chris) | + |
| Gas production from glucose | − |
| Production of acid from carbohydrate | |
| Adonitol | − |
| L(+) Arabinose | + |
| Cellobiose | + |
| Dulcitol | − |
| Meso-erythritol | − |
| Fructose | + |
| D-Galactose | + |
| D-Glucose | + |
| Glycerine | (+) |
| Inositol | − |
| Inulin | − |
| Lactose | + |
| Maltose | + |
| Mannitol | + |
| Mannose | + |
| Melibiose | + |
| Melezitose | − |
| Raffinose | + |
| L(+) Rhamnose | − |
| D-Ribose | + |
| Salicin | + |
| L-Sorbose | − |
| Sorbitol | − |
| Starch | + |
| Saccharose | + |
| Xylose | − |
| Trehalose | + |
| Hemolysis (API 20 STREP) | − |

Based on the above mycological characteristics the novel microorganism of this invention can be summarized as a gram positive spherical or ovoid microorganism; existing as single, pairs, or long-chained; incapable of producing catalase or oxidase; fermentatively decomposing carbohydrates to produce acids; non-motile, incapable of producing spores; and having a size of 0.8 to 1.0 μm.

According to the description in *Bergey's Manual of Determinative Bacteriology* (8th edition), the microorganism is judged as belonging to the genus Streptococcus. Microorganisms belonging to the genus Streptococcus (hereinafter referred to from time to time simply as "S.") can be grouped according to their capability to grow at 10° C. and 45° C., grow in a 0.1% methylene blue milk medium, decompose gelatin, exhibit salt resistance, and the like. A comparison of major strains belonging to the genus Streptococcus and the microorganism of this invention with respect to these characteristics is summarized in the table below. The microorganisms used for comparison were:

(1) S. pyocenes
(2) S. ecu
(3) S. equi
(4) S. pneumoniae
(5) S. salivaris
(6) S. bovis
(7) S. faecalis
(8) S. faecium
(9) S. lactis

| Microorganism | (1) | (2) | (3) | (4) | (5) | (6) | (7) | (8) | (9) | Microorganism of this invention |
|---|---|---|---|---|---|---|---|---|---|---|
| Gram staining | + | + | + | + | + | + | + | + | + | + |
| Growth at 10° C. | − | − | − | − | − | − | + | + | + | + |
| Growth at 45° C. | − | − | − | − | + | + | + | + | − | + |
| Growth in 0.1% methylene blue | − | − | − | − | − | − | + | + | + | + |
| Gelatin decomposition | d | − | − | − | − | − | − | − | − | − |
| Starch decomposition | − | d | NT | NT | − | + | − | − | − | − |
| Hippurate decomposition | − | − | − | NT | − | d | + | NT | d | + |
| Esculin decomposition | + | d | − | NT | + | + | + | + | d | + |
| Arginine decomposition | + | + | + | NT | − | − | + | + | + | + |
| Salt resistance (at 6.5%) | − | − | − | − | − | − | + | + | − | − |
| Growth at pH 9.6 | − | − | − | − | − | − | + | + | − | + |

(from Bergey's Manual; 8 edition)

From the above comparison the microorganism of the present invention is judged to be a strain similar to S. faecalis, S. faecium, and S. lactis. These three strains and the microorganism of the present invention are compared in more detail in the following table.

| Microorganism | S. faecalis | S. faecium | S. lactis | Microorganism of this invention |
|---|---|---|---|---|
| Size | 0.5–1.0 | 0.5–1.0 | 0.5–1.0 | 0.5–1.0 × 1.0 |
| Gram staining | + | + | + | + |
| Growth at 10° C. | + | + | + | + |
| Growth at 45° C. | − | + | + | + |
| Growth in 0.1% methylene blue | + | + | + | + |
| Gelatin decomposition | − | − | − | − |
| Starch decomposition | − | − | − | − |
| Hippurate decomposition | d | d or + | d | + |
| Esculin decomposition | d | + | + | + |
| Arginine decomposition | + | + | + | + |
| Salt resistance (at 6.5%) | − | + | + | − |
| Growth at pH 9.6 | − | + | + | + |
| Utilization of citric acid |  | + | − | − |
| Acid production |  |  |  |  |
| Glucose | + | + | + | + |
| Maltose | + | + | + | + |
| Lactose | + | + | + | + |
| Xylose | d | d |  | − |
| Arabinose | d | − | d or + | + |
| Sucrose | d | d | d | + |
| Trehalose | d | + | + | + |
| Mannitol | d | + | d | + |
| Salicin | d | + |  | + |
| Raffinose | − | − | d | + |
| Inulin | − | − | d | + |
| Glycerine | − | + | + | + |
| Sorbitol | − | + | d or − | − |
| Inositol |  |  | − | − |
| Melezitose |  | + | − | − |

| Microorganism | S. faecalis | S. faecium | S. lactis | Microorganism of this invention |
|---|---|---|---|---|
| Melibiose | | − | + | + |

According to the above comparison, the microorganism of this invention is very similar to *S. faecium*. It is, however, different from *S. faecium* with respect to Hippurate decomposition ability and salt resistance (6.5%), features which are indicative of microorganisms belonging to the genus Streptococcus. This microorganism was, therefore, identified as a microorganism belonging to the genus Streptococcus, and was named Streptococcus sp. GPOS-53 and deposited with the Fermentation Research Institute, Agency of Industrial Science and Technology [Deposition No. 2120, FERM BF-2120].

The method of obtaining DNA induced by the gene-dominating microorganism is now illustrated. Any of the above-mentioned gene-donating microorganism is first cultured in a liquid culture medium under aeration for 1 to 3 days. The culture broth is subjected to configuration to collect the cells, following which the cells are lysed to produce a bacteriolysis containing GPO gene. Treatment with a cell wall lysing enzyme such as lysozyme or β-glucanase is used for the bacteriolysis, in combination, as required, with other enzymes such as protease or a surface active agent such as sodium laurylsulfate. In addition, physical digestion of cell walls by means of freeze-thawing or French press, for example, may be employed together with the lysate.

Conventional methods of purification, including, for example, deproteinization by phenol extraction, protease treatment, ribonuclease treatment, alcohol precipitation, and centrifugation, can be applied either independently or in combination for separating and purifying DNA from the bacteriolysis.

Digestion of the DNA of the microorganism thus separated and purified can be carried out by means of treatment with ultrasonic waves or restriction endonucleases. In order to ensure ready joining of the DNA fragments and the vector DNA, however, the use of restriction endonucleases, especially type II endonuclease acting on a specific nucleotide sequences such as EcoR I, Hind III, BamH I, or BamH II, is preferable.

Desirable vectors employed are those reconstructed for use as a genetic recombinant DNA through artificial treatment of a phage or a plasmid DNA which is capable of growing autonomously in host bacterial cells.

When *Escherichia coli* is used as the host microorganism, for example, λgt. λC, λgt. λB, or the like can be used as a phage vector.

As a plasmid, pBR322, pBR325, pACYC184, pUC12, pUC13, pUC18, pUC19, or the like is used when *Escherichia coli* is the host microorganism, while pUB110, pC194, or the like is used when *Bacillus subtilis* is the host microorganism. In addition, shuttlevectors which can autonomously grow in either Gram-positive and Gram-negative microorganism host bacterial cells may be employed, for instance, in either or both *Escherichia coli* and *Saccharomyces cerevisiae*. These vectors are desirably digested by using the same restriction endonuclease as that used in breaking the above-mentioned GPO gene-donating microorganism DNA.

A conventional ligation method using a DNA ligase can be employed to join the bacterial DNA and the vector fragment. For instance, the cohesive end of the bacterial DNA and that of the vector fragment are first annealed, and then recombinant DNA from the bacterial DNA and the vector fragment can be prepared by the action of a suitable DNA ligase. If required, the annealed bacterial DNA—vector fragment is introduced into the host microorganism to produce the recombinant DNA with the aid of on in vivo DNA ligase.

Any microorganism which allows autonomic and stable growth of the recombinant DNA and is capable of expressing the character of the foreign DNA can be used as a host bacterium. Examples of such microorganisms include *Escherichia coli* DH1, *Escherichia coli* HB101, *Escherichia coli* W3110, *Escherichia coli* C600, and the like when *Escherichia coli* is used as the host bacterium.

Introducing the recombinant DNA into the host microorganism may be performed in the presence of calcium ion when the host microorganism is a bacterium belonging to the genus Escherichia. When a bacterium belonging to the genus Bacillus is used as the host microorganism, a competent cell method or an electrical fusion introduction method to introduce ribosome recombinant DNA into a protoplast host microorganism can be used. A micro-injection method can also be used.

Introducing the desired DNA into the host microorganism can be detected by means of screening using a drug resistance marker of the vector and GPO activity at the same time. For instance, those bacteria which grow on a selective culture medium based on the drug resistance marker and which produce GPO can be selected.

Recombinant DNA possessing the GPO gene once selected in this manner may be easily extracted from the transformant for introduction into another host bacterium. Alternatively, a GPO gene DNA can be digested using a restriction endonuclease or the like from a recombinant DNA possessing a GPO gene, and is joined with a terminal of a lineared vector obtained in a similar manner, thus producing a recombinant DNA molecule having novel characteristics. This can be then introduced into other host microorganisms.

DNA encoding a GPO mutein possessing substantial GPO activity means a mutated DNA produced by a genetic engineering technique from a GPO gene of this invention. This mutation can be introduced into the gene using various genetic engineering techniques, including a site specific mutagenesis method and a method for substituting a specific DNA fragment of the aimed gene with a mutated DNA fragment. Among from muteins thus prepared, those GPO mutein DNAs having especially desirable characteristics can be joined with a vector to produce recombinant DNA, which is then introduced into a host microorganism to produce a GPO mutein.

The base sequence of the DNA of this invention prepared by the method described above can be determined by the di-deoxy method [*Science*, 214, 1205–1210 (1981)]. For example, the base sequence of a GPO gene in a plasmid prepared using the strain Streptococcus sp. GPOS-53 belonging to a GPO gene-donating microorganism and *Escherichia coli* as a host bacterium is represented by the following formula (I):

```
X-TTTTCAAACAAGACAAGACAAGATAGCATTCAAAAAATGCAGCAAGAAGAATTGGAT
CTGTTGATCATCGGTGGCGGAATCACTGGTGCCGGTGTGGCAGTCCAGGCAGCAGCATCA
GGAATCAAAACAGGATTGATCGAAATGCAAGATTTTGCAGAAGGGACGTCCTCTCGCTCG
ACCAAACTTGTGCATGGCGGTATTCGTTATCTGAAAACATTTGATGTGGAAGTAGTAGCT
GACACAGTTGGTGAACGTGCAGTCGTACAAGGTATTGCCCCACACATCCCAAAACCAGAT
CCAATGCTTTTACCAATCTATGAAGATGAAGGAGCAACAACCTTCAATATGTTCTCTGTC
AAAGTAGCAATGGACCTTTACGACAAACTGGCAAATGTGACAGGAACTAAATATGAGAAC
TATACCCTCACACCAGAAGAAGTATTGGAAAGAGAACCATTTTTGAAAAAAGGAAGGCTA
AAAGGT GCAGGTGTTTATCTGGATTTCCGCAACAATGATGCCCGTTTAGTGATCGATAAT
ATCAAAAAGGCTGCAGAAGATGGGGCTTATCTAGTAAGTAAAATGAAAGCGGTTGGCTTT
TTATATGAGGGCGATCAAATCGTTGGTGTCAAAGCTCGTGATCTGCTGACAGATGAAGTG
ATAGAGATCAAAGCAAAATTAGTGATCAATACGAGTGGTCCTTGGGTAGATAAAGTACGG
AACTTGAATTTTACGCGTCCAGTCTCTCCTAAAATGCGTCCAACCAAAGGGATCCATTTA
GTCGTAGATGCGAAAAAACTGCCTGTACCGCAACCCACATACTTCGATACAGGAAAACAA
GATGGGCGGATGGTTTTTGCTATCCCAAGAGAAAACAAGACTTACTTTGGTACGACAGAT
ACGGATTACCAAGGAGACTTTACGGATCCAAAAGTCACACAAGAAGACGTGGATTATCTA
TTGGATGTAATCACCCATCGCTATCCAGAAGCAAATATCACATTGGCAGATATCGAAGCA
AGCTGGGCAGGGCTTCGTCCACTATTGATTGGTAATTCTGGTTCTGATTATAATGGTGGA
GATAATGGATCGATTTCAGACAAGAGCTTCAATAAAGTGGTTGATACAGTAAGTGAATAT
AAGGAAAATAAAGTTTCTCGTGCTGAAGTAGAAGATGTGTTGAACCATTTGGAAAACAGC
CGCGACGAAAAAGCACCTTCTACGATTTCCAGAGGGTAGTTCTTTAGAAAGAGAACCAGAT
GGCTTGTTGACTTTATCAGGTGGGAAAATCACTGATTACCGTAAGATGGCAGAAGGAGCT
TTACGATTGATTCGTCAGCTGTTAAAAGAAGAATACGGAATAGAGACGAAAGAAATCGAC
TCTAAAAAATATCAGATTTCAGGTGGAAACTTCGATCCAACGAAATTAGAAGAAACAGTG
ACGGAATTAGCAAAAGAAGGAGTAGCAGCCGGTTTAGAGGAAGAAGATGCTACTTATATC
GCTGATTTTTACGGGACTAATGCTCGACGTATGTTTGAATTAGCAAAAGAAATGGCACCT
TATCCTGGTTTGAGTCTCGCTGAGTCAGCTCGGTTACGTTATGGCTTAGAAGAAGAAATG
GTTTTAGCTCCAGGTGATTATCTCATTCGTCGTACGAATCATCTGTTGTTTGAACGAGAT
CAGCTGGATGAGATCAAGCAACCTGTGATCGATGCAATTGCTGAGTATTTTGGGTGGACA
GAAGAAGAGAAGGCGCAACAGACTAAACGTTTAGAAGCATTGATCGCAGAATCAGATCTG
CGGGAACTAAAGGGGGAGAAA-Y
``` wherein X represents a codon other than TAA, TAG, or TGA, or a 5'-terminal group, and Y represents a codon or a 3'-terminal group.

In the above formula (I), the codon represented by X may be any codon so long as the same codes for an amino acid. In addition, X may possess at its 5'-end one or more codons encoding an amino acid. Preferable examples of X are ATG or a polydeoxyribonucleic acid corresponding to a signal peptide. The codon represented by Y can be any codon selected from translation termination codons and codons encoding an amino acid. Y may possess at its 3'-end one or more codons encoding an amino acid, provided that in this case it is desirable that a translation termination codon be provided at the 3'-end of these codons.

The amino acid sequence of the polypeptide produced through the expression of the DNA of this invention can be predicted from the base sequence of the DNA. The amino acid sequence of the portion constituting the N-terminal of said polypeptide can be determined through the method discussed below. A GPO gene-donating microorganism capable of producing GPO is first cultured in a nutrient medium to produce and accumulate GPO in the cells. The cultured cells were collected from the broth by filtration, centrifugation, or the like means. The collected cells were then destroyed either by mechanical means or enzymatic means using lysozyme or the like, and to the lysate EDTA and/or a suitable surface active agent were added, as required, to solubilize and separate GPO as an aqueous solution. This aqueous solution of GPO is then condensed or, without being condensed, subjected to ammonium sulfate fractionation, gel filtration, adsorption chromatography, or ion exchange chromatography to obtain high purity GPO. The amino acid sequence of the portion constituting the N-terminal of the GPO peptide is determined for this highly purified GPO using a liquid phase protein sequencer (Beckman System 890ME, manufactured by Beckman, Inc.). In this manner, it was confirmed that the amino acid sequence of said portion was identical to the N-terminal amino acid sequence of GPO obtained by a genetic engineering technique. The amino acid sequence determined in this way from the above base sequence is represented by the following formula (II):

A—PheSerAsnLysThrArgGlnAspSerIleGlnLysMetGlnGlnGlu
GluLeuAspLeuLeuIleIleGlyGlyGlyIleThrGlyAlaGlyValAlaVal
GlnAlaAlaAlaSerGlyIleLysThrGlyLeuIleGluMetGlnAspPheAla
GluGlyThrSerSerArgSerThrLysLeuValHisGlyIleArgTyrLeu
LysThrPheAspValGluValValAlaAspThrValGlyGluArgAlaVal
ValGlnGlyIleAlaProHisIleProLysProAspProMetLeuLeuProIle
TyrGluAspGluGlyAlaThrThrPheAsnMetPheSerValLysValAla
MetAspLeuTyrAspLysLeuAlaAsnValThrGlyThrLysTyrGluAsn
TyrThrLeuThrProGluGluValLeuGluArgGluProPheLeuLysLys
GlyArgLeuLysGlyAlaGlyValTyrLeuAspPheArgAsnAsnAspAla
ArgLeuValIleAspAsnIleLysLysAlaAlaGluAspGlyAlaTyrLeuVal
SerLysMetLysAlaValGlyPheLeuTyrGluGlyAspGlnIleValGly
ValLysAlaArgAspLeuLeuThrAspGluValIleGluIleLysAlaLysLeu
ValIleAsnThrSerGlyProTrpValAspLysValArgAsnLeuAsnPhe
ThrArgProValSerProLysMetArgProThrLysGlyIleHisLeuValVal
AspAlaLysLysLeuProValProGlnProThrTyrPheAspThrGlyLys
GlnAspGlyArgMetValPheAlaIleProArgGluAsnLysThrTyrPhe
GlyThrThrAspThrAspTyrGlnGlyAspPheThrAspProLysValThr
GlnGluAspValAspTyrLeuLeuAspValIleThrHisArgTyrProGlu
AlaAsnIleThrLeuAlaAspIleGluAlaSerTrpAlaGlyLeuArgProLeu
LeuIleGlyAsnSerGlySerAspTyrAsnGlyGlyAspAsnGlySerIleSer
AspLysSerPheAsnLysValValAspThrValSerGluTyrLysGluAsn
LysValSerArgAlaGluValGluAspValLeuAsnHisLeuGluAsnSer
ArgAspGluLysAlaProSerThrIleSerArgGlySerSerLeuGluArg
GluProAspGlyLeuLeuThrLeuSerGlyGlyLysIleThrAspTyrArg
LysMetAlaGluGlyAlaLeuArgLeuIleArgGlnLeuLeuLysGluGlu
TyrGlyIleGluThrLysGluIleAspSerLysLysTyrGlnIleSerGly
GlyAsnPheAspProThrLysLeuGluGluThrValThrGluLeuAlaLys
GluGlyValAlaAlaGlyLeuGluGluGluAspAlaThrTyrIleAlaAsp
PheTyrGlyThrAsnAlaArgArgIlePheGluLeuAlaLysGluMetAla
ProTyrProGlyLeuSerLeuAlaGluSerAlaArgLeuArgTyrGlyLeu
GluGluGluMetValLeuAlaProGlyAspTyrLeuIleArgArgThrAsn
HisLeuLeuPheGluArgAspGlnLeuAspGluIleLysGlnProValIle
AspAlaIleAlaGluTyrPheGlyTrpThrGluGluGluLysAlaGlnGln
ThrLysArgLeuGluAlaLeuIleAlaGluSerAspLeuArgGluLeuLys
GlyGluLys—B wherein A represents an amino acid residue or a hydrogen atom and B represents an amino acid residue or an —OH group. In the amino acid sequence expressed by formula (II) the amino acid residue represented by A may be one or more amino acids. Preferred examples of A are a hydrogen atom, a Met, or a signal polypeptide. The group represented by B may be either an acid amide or one or more amino acid residues.

The transformant thus obtained, when cultured in a nutrient medium, can produce a large amount of GPO in a stable manner.

Culturing of the transformant is conducted under the conditions determined while taking the nutrient—physiological characteristics of the host microorganism into consideration. In most of the cases liquid culturing is employed. For industrial scale production, however, culturing under deep aerobic stirring conditions is more advantageous. A wide variety of nutrients conventionally used for bacterial culture can be used for culturing the host microorganism. Specifically, any carbon compounds which are utilizable can be used as carbon sources. These include, for example, glucose, sucrose, lactose, maltose, fructose, molasses, and the like. As nitrogen sources, any available nitrogen compounds can be employed, inclusive of peptones, meat extracts, yeast extracts, casein hydrolyzates, and the like. Other ingredients, including salts such as phosphates, carbonates, and sulfates, as well as salts of magnesium, calcium, potassium, iron, manganese, zinc, and the like, and certain types of amino acids or vitamins, may be used as appropriate. The process does not need the use of GPO-inducing substances such as glycerol, ascorbic acid, α-keto acid, and the like, which are essential in the conventional process for producing GPO.

The culturing temperature can be varied in a range in which the bacteria can grow and produce GPO. A preferable temperature range is 20°–42° C. for *Escherichia coli*. The culturing time may be varied to some degree depending on the culturing conditions. Basically, the culturing is terminated at the time when the yield of GPO reaches maximum. In usual practice, this takes about 12–48 hours. It is possible to change the pH of the culture media within the range in which the bacteria can grow and produce GPO. The especially preferable pH range is about 6–8.

GPO may be served for use in the form of a culture broth as it contains bacteria. GPO contained in the culture broth, however, is generally used after being separated from the cells by filtration, centrifugation, or the like means. When GPO is contained within the cells, the cells are first separated by means of filtration or centrifugation. The collected cells are then digested either by mechanical means or enzymatic means using lysozyme or the like, and to the digested bacteria a chelating agent such as EDTA and/or a suitable surfactant is added, as required, to solubilize GPO, thus allowing the collection of GPO as an aqueous solution.

The solutions containing GPO thus obtained are then condensed by evaporation in vacuo or by using a filter, and subjected to salting-out treatment with ammonium sulfate, sodium sulfate, or the like, or to fractional precipitation using a hydrophilic organic solvent such as methanol, ethanol, acetone, or the like. The precipitate is dissolved in water, and the solution is dialyzed through a semipermeable membrane to eliminate low molecular weight impurities. Alternatively, the precipitate is refined by means of gel filtration, chromatography, ion-exchange chromatography or the like. Purified GPO is produced from the GPO-containing solution obtained by using these various means through vacuum evaporation, lyophilization, or the like.

The activity of the GPO thus prepared is measured according to the following method:

Reaction mixture:
200 mM PIPES-NaOH buffer (pH 6.5)
300 mM L-α-glycerophosphate
5 μ/ml peroxidase
1.5 mM 4-aminoantipirin
0.05% Triton X-100
1.0 mM DAOS [3,5-dimethoxy-N-ethyl-N-(2-hydroxy-3-sulfopropyl)-aniline sodium salt]

Add 1.0 ml of the reaction mixture into a test tube and equibrate the temperature at 37° C. Add 0.02 ml of enzyme solution and incubate at 37° C. for 5 minutes. Stop the reaction by adding 2.0 ml of 0.5% SDS and measure the absorbance at 600 nm (As). Repeat the procedure using dilution water in place of the enzyme solution (Ab). The activity of the substance to produce 1μ mole of hydrogen peroxide per minute was taken as 1 unit (U) according to the following equation.

$$\text{Units/mg} = \frac{\Delta A}{16.8 \times \frac{1}{2}} \times \frac{3.02}{0.02} \times \frac{1}{X} \times \frac{1}{5}$$

wherein $\Delta A = As - b$, 16.6 is the molecular extinction coefficient for quinone coloring substance (cm$^2$/μ mole) and X represents the concentration of GOP in the enzyme solution (mg/ml).

In the description of this specification, amino acids, peptides, nucleic acids, and nucleic acid-related compounds are abbreviated according to the prevailing standards. Some examples of the abbreviation are listed below. All designations of amino acids denote the L-isomers.

DNA: Deoxyribonucleic acid
RNA: Ribonucleic acid
A: Adenine
T: Thymine
G: Guanine
C: Cytosine
Ala: Alanine
Arg: Arginine
Asn: Asparagine
Asp: Aspartate
Cys: Cysteine
Gln: Glutamine
Glu: Glutamate
Gly: Glycine
His: Histidine
Ile: Isoleucine
Leu: Leucine
Lys: Lysine
Met: Methionine
Phe: Phenylalanine
Pro: Proline
Ser: Serine
Thr: Threonine
Trp: Tryptophan
Tyr: Tyrosine
Val: Valine Other features of the invention will become apparent in the course of the following description of the exemplary embodiments which are given for illustration of the invention and are not intended to be limiting thereof.

EXAMPLES

Example 1 [Preparation of Chromosomal DNA]

A chromosomal DNA was prepared from strain Streotococcus sp. GPOS-53 (FERM BP-2120) by the following method. The strain was cultured with shaking overnight at 37° C. in 150 ml of Brain Heart Infusion medium (produced by Difco Co.; hereinafter abbreviated as "BHI medium"). The cultured broth was centrifuged at 3,000 rpm for 10 minutes to collect the cells. The cells were suspended into 5 ml of a solution containing 10% saccharose, 50 mM Tris hydrochloric acid (pH 8.0), and 50 mM EDTA. To the suspension, 1 ml of lysozyme solution (10 mg/ml) was added, and the mixture was incubated at 37° C. for 15 minutes, followed by the addition of 1 ml of 10% SDS (sodium dodecylsulfate). To the suspension thus obtained an equal volume of a mixed solvent of chloroform and phenol (1:1) was added, and the mixture was stirred and centrifuged at 10,000 rpm for 3 minutes to separate the water and solvent layers. To the separated water layer, a 2-fold volume of ethanol was added slowly, and the mixture was stirred slowly with a glass rod so as to cause the DNA to wind around the rod. The DNA separated in this manner was dissolved into 10 ml of a solution containing 10 mM Tris hydrochloric acid (pH 8.0) and 1 mM EDTA (such a solution is hereinafter referred to as "TE"). This solution was treated with an equal volume of chloroform—phenol mixed solvent, and was again centrifuged to separate the water layer. To this solution, a 2-fold volume of ethanol was further added, and the DNA was again separated from the mixture in the same manner as described above. This DNA was then dissolved into 2 ml of TE.

Example 2 [Preparation of pACYC 184 Plasmid DNA]

Escherichia coli pM191 carrying pACYC 184 therein [J. Bacteriol, 134, 1141 (1981); ATCC37033] was cultured by shaking in 1 liter of BHI medium (produced by Difco Co.). When the turbidity of the broth reached $OD_{660} = 1.0$, spectinomycin was added at a final concentration of 300 µg/ml. Shaking of the broth at 37° C. was continued for at least 16 hours. Upon termination of the shake culturing the broth was centrifuged at 3,000 rpm for 10 minutes to collect the cells. The plasmid DNA, collected from the cells, was prepared according to the lysozyme—SDS method and the cesium chloride—ethidium bromide method [Maniatis et al, *Molecular Cloning*, 86-94, Cold Spring Harbor (1982)].

Example 3 [Construction of Plasmid pGPOS1 having the L-α-glycerophosphate oxidase Gene]

(1) Two (2) µl (about 0.5 µg) of Strectococcus sp chromosomal DNA prepared in Example 1, 1 µl of a 10-fold concentration of M-buffer [Maniatis et al., *Molecular Cloning*, 104, Cold Spring Harbor (1982)], 1 µl of Hind III (1.0 unit/µl; produced by Takara Shuzo Co., Ltd.), and 6 µl of water were mixed and incubated at 37° C. for 1 hour for digestion. Plasmid pACYC 184 DNA (about 0.3 µg) was digested separately using Hind III according to a similar method. To this was added 0.6 unit of alkaline phosphatase (produced by Takara Shuzo Co., Ltd.; hereinafter referred to as "BAP") and the mixture was incubated at 65° C. for 1 hour. The two DNA solutions thus digested with Hind III were mixed together, and to this mixed DNA solution, 0.1 volume of 3 M sodium acetate was added. Subsequently, the solution was treated with an equal volume of a chloroform-phenol mixed solvent and centrifuged to separate the water layer. To this a 2-fold amount of ethanol was added, and the DNA was precipitated by means of centrifugation and dried in vacuo. The dried DNA was dissolved into 89 µl of water, and to this 10 µl of a 10-fold concentration of ligation buffer [0.5 M Tris hydrochloric acid (pH 7.6), 0.1 M MgCl₂, 0.1 M dithiothreitol, 10 mM spermidine, 10 mM ATP] and 1 µl of T4 DNA ligase (350 unit; produced by Takara Shuzo Co., Ltd.) were added and mixed, and the mixture was allowed to stand at 4° C. overnight. This DNA solution was treated with a chloroform-phenol mixture, and the DNA was precipitated with ethanol, dried in vacuo, and dissolved into 10 µl of TE.

(2) *Escherichia coli* DH 1 (*J. Molecular Biology*, 557 (1983); provided by Genetic Stock Center; Yale University Medical Department] was cultured in 100 ml of BHI medium, collected during logarithmic growth phase by centrifugation (10,000 rpm, 2 minutes), and suspended into 40 ml of an ice-cooled solution containing 30 mM potassium acetate, 100 mM RbCl, 10 mM CaCl₂, 50 mM MnCl", and 15% glycerine (pH 5.8). After standing at 0° C. for 5 minutes, the suspension was centrifuged to remove the supernatant. The cells were suspended into 4 ml of a solution containing 10 mM MOPS buffer (produced by Dotite Co.), 75 mM CaCl₂, 10 mM RbCl, and 15% glycerine (pH 6.5), and the suspension was left at 0° C. for 5 minutes to obtain competent cells.

(3) To 200 µl of the cell suspension 10 µl of the DNA solution prepared in (1) above were added. After the mixture was allowed to stand at 0° C. for 30 minutes, 1 ml of BHI medium was added to it, and the mixture was kept at 37° C. for 90 minutes. An aliquot of the mixture (0.1 ml) was spread on a BHI agar plate containing 25 µg/ml of chloramphenicol, and cultured overnight at 37° C. to produce transformants. These transformants were replicated on a GPOS medium plate (composition: peptone: 5 g, meat extract: 2 g, yeast extract: 5 g, NaCl: 1 g, K₂HPO₄: 1 g, MgSO₄: 0.5 g, peroxidase: 500 IU, dianisidine: 0.1 g, potassium glycerophosphate: 15 g, agar: 15 g, distilled water: 1 liter; pH 7.0), and was further cultured overnight at 37° C.

About 5,000 transformants thus produced were investigated in order to obtain 4 colonies having charcoal-colored peripheries. One of the four strains was named *Escherichia coli* DHI pGPOS1 (Deposited with the Fermentation Research Institute, Agency of Industrial Science and Technology; Deposition No. 9493, FERM BP-2133). This strain was cultured after purification in BHI medium overnight at 37° C. to determine its GPO productivity according to the GPO activity measurement method described above. As a result, the GPO activity was found to be a 0.5 µ/ml.

The plasmid DNA contained in the strain was separated according to the same method as in Example 2, and the plasmid containing the GPO gene and the pACYC 184 gene was named pGPOS1.

Figure 1:
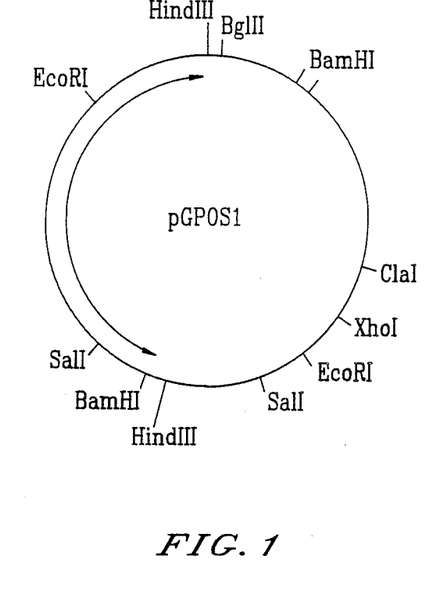
FIG. 1 is a schematic drawing showing the construction of plasmid pGPOS1.

Example 4 [Mapping of pGPOS1 and Determination of the Base Sequence of the GPO Gene]

pGPOS1 plasmid DNA was prepared from the *Escherichia coli* DHI pGPOS1 strain in the same manner as that employed for the preparation of pACYC 184. A cleavage map of the pGPOS1 plasmid DNA thus obtained was prepared using the endonucleases BamH I, Bgl II, Cta I, EcoR I, Pst I, Sal I, and Xho I (all produced by Takara Shuzo Co., Ltd.). The results are shown in FIG. 1. The base sequence of the DNA comprising GPO gene was determined by means of the di-deoxy method [*Science*, 214, 1205–1210 (1981)] using M13 phage. The base sequence of the GPO gene was that having ATG for X and TAA for Y in formula (I). The amino acid sequence determined from the base sequence was that having Met for A and —OH for B in formula (II).

Example 5 [Preparation of L-α-glycerophosphate oxidase using *Escherichia coli* DHI pGPOS1 strain]

*Escherichia coli* DHI pGPOS1 was cultured in 20 l of BHI medium using a jar fermenter at 37° C. for 18 hours. The cells thus produced were collected by centrifugation at 5,000 rpm for 10 minutes, washed with 2 l of physiological saline, and suspended into 2 l of a 10 mM phosphate buffer (pH 7.0). To this suspension lysozyme, EDTA-2Na, and Triton X-100 were added in such amounts that their respective concentrations in the mixture were 1 mg/ml, 2 mM, and 0.1%. After incubation at 37° C. for 30 minutes, the mixture was centrifuged at 5,000 r.p.m. for 10 minutes to separate the supernatant.

The supernatant (1.9 l) was subjected to salting-out with ammonium sulfate (40–66%), and the precipitate was collected. This precipitate was dissolved in 200 ml of 10 mM phosphate buffer (pH 7.0, containing 10 μM FAD), and the solution was submitted to desalting treatment over Sephadex G-25. Active fractions were collected by means of ion-exchange chromatography using DEAE-Sepharose CL-6B, desalted, and lyophilyzed to produce 0.395 g of L-α-glycerophosphate oxidase in a powdery form (40 μ/mg, yield: 27%).

The physicochemical characteristics of L-α-glycerophosphate oxidase thus obtained were as follows:

(a) Action:
catalyses the following reaction:

L-α-glycerophosphate+O$_2$→dihydroxyacetone phosphate+H$_2$O$_2$ (b) Substrate specificity:
exhibits a substrate specificity for L-α-glycerophosphate.

(c) Optimum pH:
GOP was reacted at each pH; glycin-hydrochloric acid buffer (pH 2.0–5.0), acetic acid buffer (pH 4.0–6.0), 3,3-dimethyl glutamic acid-NaOH buffer (pH 5.0–7.0), phosphate buffer (pH 6.0–8.0), and Tris-hydrochloric acid buffer (pH 7.0–9.0). As a result the optimum pH of the enzyme was found to exist in the range of 5.5–7.5.

(d) pH Stability:
The enzyme solutions (5.0 μ/ml) were prepared using 100 mM acetic acid (pH 4.0–6.0), 100 mM 3,3-dimethyl glutamic acid-NaOH (pH 5.0–7.0), 100 mM phosphate (pH 6.0–8.0), and 100 mM Tris-hydrochloric acid buffers (pH 7.0–9.0) all at 100 mM. Each solution was incubated at 50° C. for 5 minutes to determine the residual activity of the enzyme. As a result, the enzyme was found to be stable at pH 6.0–8.0.

(e) Km value: 5.5±0.5 mM (for L-α-glycerophosphate)

(f) Isoelectric point: 4.0±0.5 (measured by a focusing electrophoresis using an ampholine carrier)

(g) Thermal stability:

The enzyme solutions (5.0 μ/ml) prepared using 0.1 M phosphate buffer (pH 6.5) were incubated at various temperatures for 5 minutes, and the residual activity of each of the solution was measured. As a result, the enzyme was found to exhibit 100% activity up to 40° C.

(i) Enzyme stability over time:
Enzyme solutions (5.0 μ/ml) was prepared using 0.1 M MES-NaOH buffer (pH 6.5) and incubated at 37° C. for different periods of time. As a result of measurement of the residual activity, the enzyme was found to exhibit at least 90% activity after 24 hours. This stability in the solution represents the stability of the enzyme in conditions encountered in actual clinical diagnosis, and demonstrates that the enzyme is very useful.

The use of the DNA and the transformant of this invention ensures an efficient production of L-α-glycerophosphate oxidase without the need for the addition of GPO-inducing substances such as glycerol, ascorbic acid, or the like. In addition, the invention has clarified characteristics of the GPO gene.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. Isolated DNA having a base sequence encoding a polypeptide having an amino acid sequence starting from the N-terminal end:

A—PheSerAsnLysThrArgGlnAspSerIleGlnLysMetGlnGlnGlu
GluLeuAspLeuLeuIleIleGlyGlyGlyIleThrGlyAlaGlyValAlaVal
GlnAlaAlaAlaSerGlyIleLysThrGlyLeuIleGluMetGlnAspPheAla
GluGlyThrSerSerArgSerThrLysLeuValHisGlyGlyIleArgTyrLeu
LysThrPheAspValGluValValAlaAspThrValGlyGluArgAlaVal
ValGlnGlyIleAlaProHisIleProLysProAspProMetLeuLeuProIle
TyrGluAspGluGlyAlaThrThrPheAsnMetPheSerValLysValAla
MetAspLeuTyrAspLysLeuAlaAsnValThrGlyThrLysTyrGluAsn
TyrThrLeuThrProGluGluValLeuGluArgGluProPheLeuLysLys
GlyArgLeuLysGlyAlaGlyValTyrLeuAspPheArgAsnAsnAspAla
ArgLeuValIleAspAsnIleLysLysAlaAlaGluAspGlyAlaTyrLeuVal
SerLysMetLysAlaValGlyPheLeuTyrGluGlyAspGlnIleValGly
ValLysAlaArgAspLeuLeuThrAspGluValIleGluIleLysAlaLysLeu
ValIleAsnThrSerGlyProTrpValAspLysValArgAsnLeuAsnPhe
ThrArgProValSerProLysMetArgProThrLysGlyIleHisLeuValVal
AspAlaLysLysLeuProValProGlnProThrTyrPheAspThrGlyLys
GlnAspGlyArgMetValPheAlaIleProArgGluAsnLysThrTyrPhe
GlyThrThrAspThrAspTyrGlnGlyAspPheThrAspProLysValThr
GlnGluAspValAspTyrLeuLeuAspValIleThrHisArgTyrProGlu
AlaAsnIleThrLeuAlaAspIleGluAlaSerTrpAlaGlyLeuArgProLeu
LeuIleGlyAsnSerGlySerAspTyrAsnGlyGlyAspAsnGlySerIleSer
AspLysSerPheAsnLysValValAspThrValSerGluTyrLysGluAsn
LysValSerArgAlaGluValGluAspValLeuAsnHisLeuGluAsnSer
ArgAspGluLysAlaProSerThrIleSerArgGlySerSerLeuGluArg
GluProAspGlyLeuLeuThrLeuSerGlyGlyLysIleThrAspTyrArg
LysMetAlaGlyGlyAlaLeuArgLeuIleArgGlnLeuLeuLysGluGlu
TyrGlyIleGluThrLysGluIleAspSerLysLysTyrGlnIleSerGly
GlyAsnPheAspProThrLysLeuGluGluThrValThrGluLeuAlaLys
GluGlyValAlaAlaGlyLeuGluGluGluAspAlaThrTyrIleAlaAsp
PheTyrGlyThrAsnAlaArgArgIlePheGluLeuAlaLysGluMetAla
ProTyrProGlyLeuSerLeuAlaGluSerAlaArgLeuArgTyrGlyLeu
GluGluGluMetValLeuAlaProGlyAspTyrLeuIleArgArgThrAsn
HisLeuLeuPheGluArgAspGlnLeuAspGluIleLysGlnProValIle
AspAlaIleAlaAlaGluTyrPheGlyTrpThrGluGluGluLysAlaGlnGln
ThrLysArgLeuGluAlaLeuIleAlaGluSerAspLeuArgGluLeuLys
GlyGluLys—B wherein A represents an amino acid residue or a hydrogen atom and B represents an amino acid residue or an —OH group.

2. The DNA according to claim 1 having a base sequence starting from the 5'-end:

```
X-TTTTCAAACAAGACAAGACGAAGATAGCATTCAAAAAATGCAGCAAGAAGAATTGGAT
CTGTTGATCATCGGTGGCGGAATCACTGGTGCCGGTGTGGCAGTCCAGGCAGCAGCATCA
GGAATCAAAACAGGATTGATCGAAATGCAAGATTTTGCAGAAGGGACGTCCTCTCGCTCG
ACCAAACTTGTGCATGGCGGTATTCGTTATCTGAAAACATTTGATGTGGAAGTAGTAGCT
GACACAGTTGGTGAACGTGCAGTCGTACAAGGTATTGCCCCACACATCCCAAAACCAGAT
CCAATGCTTTTACCAATCTATGAAGATGAAGGAGCAACAACCTTCAATATGTTCTCTGTC
AAAGTAGCAATGGACCTTTACGACAAACTGGCAAATGTGACAGGAACTAAATATGAGAAC
TATACCCTCACACCAGAAGAAGTATTGGAAAGAGAACCATTTTTGAAAAAAGGAAGGCTA
AAAGGTGCAGGTGTTTATCTGGATTTCCGCAACAATGATGCCCGTTTAGTGATCGATAAT
ATCAAAAAGGCTGCAGAAGATGGGGCTTATCTAGTAAGTAAAATGAAAGCGGTTGGCTTT
TTATATGAGGGCGATCAAATCGTTGGTGTCAAAGCTCGTGATCTGCTGACAGATGAAGTG
ATAGAGATCAAAGCAAAATTAGTGATCAATACGAGTGGTCCTTGGGTAGATAAAGTACGG
AACTTGAATTTTACGCGTCCAGTCTCTCCTAAAATGCGTCCAACCAAAGGGATCCATTTA
GTCGTAGATGCGAAAAAACTGCCTGTACCGCAACCCACATACTTCGATACAGGAAAACAA
GATGGGCGGATGGTTTTTGCTATCCCAAGAGAAAACAAGACTTACTTTGGTACGACAGAT
ACGGATTACCAAGGAGACTTTACGGATCCAAAAGTCACACAAGAAGACGTGGATTATCTA
TTGGA TGTAATCACCCATCGCTATCCAGAAGCAAATATCACATTGGCAGATATCGAAGCA
AGCTGGGCAGGGCTTCGTCCACTATTGATTGGTAATTCTGGTTCTGATTATAATGGTGGA
GATAATGGATCGATTTCAGACAAGAGCTTCAATAAAGTGGTTGATACAGTAAGTGAATAT
AAGGAAAATAAAGTTTCTCGTGCTGAAGTAGAAGATGTGTTGAACCATTTGGAAAACAGC
CGCGACGAAAAAGCACCTTCTACGATTTCCAGAGGTAGTTCTTTAGAAAAGAGAACCAGAT
GGCTTGTTGACTTTATCAGGTGGCAAAATCACTGATTACCGTAAGATGGCAGAAGGAGCT
TTACGATTGATTCGTCAGCTGTTAAAAGAAGAATACGGAATAGAGACGAAAGAAATCGAC
TCTAAAAAATATCAGATTTCAGGTGGAAACTTCGATCCAACGAAATTAGAAGAAACAGTG
ACGGAATTAGCAAAAGAAGGAGTAGCAGCCGGTTTAGAGGAAGAAGATGCTACTTATATC
GCTGATTTTTACGGGACTAATGCTCGACGTATGTTTGAATTAGCAAAAGAAATGGCACCT
TATCCTGGTTTGAGTCTCGCTGAGTCAGCTCGGTTACGTTATGGCTTAGAAGAAGAAATG
GTTTTAGCTCCAGGTGATTATCTCATTCGTCGTACGAATCATCTGTTGTTTGAACGAGAT
CAGCTGGATGAGATCAAGCAACCTGTGATCGATGCAATTGCTGAGTATTTTGGGTGGACA
GAAGAAGAGAAGGCGCAACAGACTAAACGTTTAGAAGCATTGATCGCAGAATCAGATCTG
CGGGAACTAAAGGGGGAGAAA-Y
``` wherein X represents a codon other than TAA, TAG, or TGA, or a 5′-terminal group, and Y represents a codon or a 3′-terminal group.

3. A transformant having a DNA which is foreign with respect to the host microorganism and comprises a base sequence encoding a polypeptide having the amino acid sequence, starting from the N-terminal end;

A—PheSerAsnLysThrArgGlnAspSerIleGlnLysMetGlnGlnGlu
GluLeuAspLeuLeuIleIleGlyGlyGlyIleThrGlyAlaGlyValAlaVal
GlnAlaAlaAlaSerGlyIleLysThrGlyLeuIleGluMetGlnAspPheAla
GluGlyThrSerSerArgSerThrLysLeuValHisGlyGlyIleArgTyrLeu
LysThrPheAspValGluValValAlaAspThrValGlyGluArgAlaVal
ValGlnGlyIleAlaProHisIleProLysProAspProMetLeuLeuProIle
TyrGluAspGluGlyAlaThrThrPheAsnMetPheSerValLysValAla
MetAspLeuTyrAspLysLeuAlaAsnValThrGlyThrLysTyrGluAsn
TyrThrLeuThrProGluGluValLeuGluArgGluProPheLeuLysLys
GlyArgLeuLysGlyAlaGlyValTyrLeuAspPheArgAsnAsnAspAla
ArgLeuValIleAspAsnIleLysLysAlaAlaGluAspGlyAlaTyrLeuVal
SerLysMetLysAlaValGlyPheLeuTyrGluGlyAspGlnIleValGly
ValLysAlaArgAspLeuLeuThrAspGluValIleGluIleLysAlaLysLeu
ValIleAsnThrSerGlyProTrpValAspLysValArgAsnLeuAsnPhe
ThrArgProValSerProLysMetArgProThrLysGlyIleHisLeuValVal
AspAlaLysLysLeuProValProGlnProThrTyrPheAspThrGlyLys

-continued

GlnAspGlyArgMetValPheAlaIleProArgGluAsnLysThrTyrPhe
GlyThrThrAspThrAspTyrGlnGlyAspPheThrAspProLysValThr
GlnGluAspValAspTyrLeuLeuAspValIleThrHisArgTyrProGlu
AlaAsnIleThrLeuAlaAspIleGluAlaSerTrpAlaGlyLeuArgProLeu
LeuIleGlyAsnSerGlySerAspTyrAsnGlyGlyAspAsnGlySerIleSer
AspLysSerPheAsnLysValValAspThrValSerGluTyrLysGluAsn
LysValSerArgAlaGluValGluAspValLeuAsnHisLeuGluAsnSer
ArgAspGluLysAlaProSerThrIleSerArgGlySerSerLeuGluArg
GluProAspGlyLeuLeuThrLeuSerGlyGlyLysIleThrAspTyrArg
LysMetAlaGluGlyAlaLeuArgLeuIleArgGlnLeuLeuLysGluGlu
TyrGlyIleGluThrLysGluIleAspSerLysLysTyrGlnIleSerGly
GlyAsnPheAspProThrLysLeuGluGluThrValThrGluLeuAlaLys
GluGlyValAlaAlaGlyLeuGluGluGluAspAlaThrTyrIleAlaAsp
PheTyrGlyThrAsnAlaArgArgIlePheGluLeuAlaLysGluMetAla
ProTyrProGlyLeuSerLeuAlaGluSerAlaArgLeuArgTyrGlyLeu
GluGluGluMetValLeuAlaProGlyAspTyrLeuIleArgArgThrAsn
HisLeuLeuPheGluArgAspGlnLeuAspGluIleLysGlnProValIle
AspAlaIleAlaGluTyrPheGlyTrpThrGluGluGluLysAlaGlnGln
ThrLysArgLeuGluAlaLeuIleAlaGluSerAspLeuArgGluLeuLys
GlyGluLys—B

4. The transformant according to claim 3, wherein the base sequence of said DNA starting from the 5′-end is:

```
X-TTTTCAAACAAGACAAGACGAAGATAGCATTCAAAAAATGCAGCAAGAAGAATTGGAT
CTGTTGATCATCGGTGGCGGAATCACTGGTGCCGGTGTGGCAGTCCAGGCAGCAGCATCA
GGAATCAAAACAGGATTGATCGAAATGCAAGATTTTGCAGAAGGGACGTCCTCTCGCTCG
ACCAAACTTGTGCATGGCGGTATTCGTTATCTGAAAACATTTGATGTGGAAGTAGTAGCT
GACACAGTTGGTGAACGTGCAGTCGTACAAGGTATTGCCCCACACATCCCAAAACCAGAT
CCAATGCTTTTACCAATCTATGAAGATGAAGGAGCAACAACCTTCAATATGTTCTCTGTC
AAAGTAGCAATGGACCTTTACGACAAACTGGCAAATGTGACAGGAACTAAATATGAGAAC
TATACCCTCACACCAGAAGAAGTATTGGAAAGAGAACCATTTTTGAAAAAAGGAAGGCTA
AAAGGTGCAGGTGTTTATCTGGATTTCCGCAACAATGATGCCCGTTTAGTGATCGATAAT
ATCAAAAAGGCTGCAGAAGATGGGGCTTATCTAGTAAGTAAAATGAAAGCGGTTGGCTTT
TTATATGAGGGCGATCAAATCGTTGGTGTCAAAGCTCGTGATCTGCTGACAGATGAAGTG
ATAGAGATCAAAGCAAAATTAGTGATCAATACGAGTGGTCCTTGGGTAGATAAAGTACGG
AACTTGAATTTTACGCGTCCAGTCTCTCCTAAAATGCGTCCAACCAAAGGGATCCATTTA
GTCGTAGATGCGAAAAAACTGCCTGTACCGCAACCCACATACTTCGATACAGGAAAACAA
GATGGGCGGATGGTTTTTGCTATCCCAAGAGAAAACAAGACTTACTTTGGTACGACAGAT
ACGGATTACCAAGGAGACTTTACGGATCCAAAAGTCACACAAGAAGACGTGGATTATCTA
TTGGATGTAATCACCCATCGCTATCCAGAAGCAAATATCACATTGGCAGATATCGAAGCA
AGCTGGGCAGGGCTTCGTCCACTATTGATTGGTAATTCTGGTTCTGATTATAATGGTGGA
GATAATGGATCGATTTCAGACAAGAGCTTCAATAAAGTGGTTGATACAGTAAGTGAATAT
AAGGAAAATAAAGTTTCTCGTGCTGAAGTAGAAGATGTGTTGAACCATTTGGAAAACAGC
CGCGACGAAAAAGCACCTTCTACGATTTCCAGAGGTAGTTCTTTAGAAAAGAGAACCAGAT
GGCTTGTTGACTTTATCAGGTGGGAAAATCACTGATTACCGTAAGATGGCAGAAGGAGCT
```

```
TTACGATTGATTCGTCAGCTGTTAAAAGAAGAATACGGAATAGAGACGAAAGAAATCGAC
TCTAAAAAATATCAGATTTCAGGTGGAAACTTCGATCCAACGAAATTAGAAGAAACAGTG
ACGGAATTAGCAAAAGAAGGAGTAGCAGCCGGTTTAGAGGAAGAAGATGCTACTTATATC
GCTGATTTTTACGGGACTAATGCTCGACGTATGTTTGAATTAGCAAAAGAAATGGCACCT
TATCCTGGTTTGAGTCTCGCTGAGTCAGCTCGGTTACGTTATGGCTTAGAAGAAGAAATG
GTTTTAGCTCCAGGTGATTATCTCATTCGTCGTACGAATCATCTGTTGTTTGAACGAGAT
CAGCTGGATGAGATCAAGCAACCTGTGATCGATGCAATTGCTGAGTATTTTGGGTGGACA
GAAGAAGAGAAGGCGCAACAGACTAAACGTTTAGAAGCATTGATCGCAGAATCAGATCTG
CGGGAACTAAAGGGGGAGAAA
Y
``` wherein X represents a codon other than TAA, TAG, or TGA, or a 5'-terminal group, and Y represents a codon or a 3'-terminal group.

5. The transformant according to claim 3 which is the strain *Escherichia coli* DH1 pGPOS1 (FERM BP-2133).

6. The transformant according to claim 3, belonging to the species *Escherichia coli*.

7. A process for preparing L-α-glycerophosphate oxidase comprising:
culturing a transformant having a DNA which is foreign with respect to the host microorganism and comprises a base sequence encoding a polypeptide having the amino acid sequence starting from the N-terminal end:

A—PheSerAsnLysThrArgGlnAspSerIleGlnLysMetGlnGlnGlu
GluLeuAspLeuLeuIleIleGlyGlyGlyIleThrGlyAlaGlyValAlaVal
GlnAlaAlaAlaSerGlyIleLysThrGlyLeuIleGluMetGlnAspPheAla
GluGlyThrSerSerArgSerThrLysLeuValHisGlyGlyIleArgTyrLeu
LysThrPheAspValGluValValAlaAspThrValGlyGluArgAlaVal
ValGlnGlyIleAlaProHisIleProLysProAspProMetLeuLeuProIle
TyrGluAspGluGlyAlaThrThrPheAsnMetPheSerValLysValAla
MetAspLeuTyrAspLysLeuAlaAsnValThrGlyThrLysTyrGluAsn
TyrThrLeuThrProGluGluValLeuGluArgGluProPheLeuLysLys
GlyArgLeuLysGlyAlaGlyValTyrLeuAspPheArgAsnAsnAspAla
ArgLeuValIleAspAsnIleLysLysAlaAlaGluAspGlyAlaTyrLeuVal
SerLysMetLysAlaValGlyPheLeuTyrGluGlyAspGlnIleValGly
ValLysAlaArgAspLeuLeuThrAspGluValIleGluIleLysAlaLysLeu
ValIleAsnThrSerGlyProTrpValAspLysValArgAsnLeuAsnPhe
ThrArgProValSerProLysMetArgProThrLysGlyIleHisLeuValVal
AspAlaLysLysLeuProValProGlnProThrTyrPheAspThrGlyLys

GlnAspGlyArgMetValPheAlaIleProArgGluAsnLysThrTyrPhe
GlyThrThrAspThrAspTyrGlnGlyAspPheThrAspProLysValThr
GlnGluAspValAspTyrLeuLeuAspValIleThrHisArgTyrProGlu
AlaAsnIleThrLeuAlaAspIleGluAlaSerTrpAlaGlyLeuArgProLeu
LeuIleGlyAsnSerGlySerAspTyrAsnGlyGlyAspAsnGlySerIleSer
AspLysSerPheAsnLysValValAspThrValSerGluTyrLysGluAsn
LysValSerArgAlaGluValGluAspValLeuAsnHisLeuGluAsnSer
ArgAspGluLysAlaProSerThrIleSerArgGlySerSerLeuGluArg
GluProAspGlyLeuLeuThrLeuSerGlyGlyLysIleThrAspTyrArg
LysMetAlaGluGlyAlaLeuArgLeuIleArgGlnLeuLeuLysGluGlu
TyrGlyIleGluThrLysGluIleAspSerLysLysTyrGlnIleSerGly
GlyAsnPheAspProThrLysLeuGluGluThrValThrGluLeuAlaLys
GluGlyValAlaAlaGlyLeuGluGluGluAspAlaThrTyrIleAlaAsp
PheTyrGlyThrAsnAlaArgArgIlePheGluLeuAlaLysGluMetAla
ProTyrProGlyLeuSerLeuAlaGluSerAlaArgLeuArgTyrGlyLeu
GluGluGluMetValLeuAlaProGlyAspTyrLeuIleArgArgThrAsn
HisLeuLeuPheGluArgAspGlnLeuAspGluIleLysGlnProValIle
AspAlaIleAlaGluTyrPheGlyTrpThrGluGluGluLysAlaGlnGln
ThrLysArgLeuGluAlaLeuIleAlaGluSerAspLeuArgGluLeuLys
GlyGluLys—B wherein A represents an amino acid residue or a hydrogen atom and B represents an amino acid residue or an —OH group, and expression sequences operable in said host, and said host microorganism is selected from the group consisting of microorganisms belonging to *Escherichia coil, Bacillus subtilis, Saccharomyces cerevisiae*, under conditions which permit expression of the genetic information of said DNA; and isolating said polypeptide.

8. The process according to claim 7, wherein the host microorganism is *Escherichia coli*.

* * * * *